United States Patent [19]

Fujii et al.

[11] Patent Number: 5,766,434
[45] Date of Patent: Jun. 16, 1998

[54] OXYGEN CONCENTRATION DETECTING DEVICE AND METHOD FOR FABRICATING THE SAME

[75] Inventors: Namitsugu Fujii, Yokkaichi; Hiromi Sano, Nagoya; Yasumichi Hotta, Mie-ken; Naoto Miwa, Tsushima; Motoaki Satou, Kariya, all of Japan

[73] Assignee: Denso Corporation, Kariya, Japan

[21] Appl. No.: 797,652

[22] Filed: Jan. 31, 1997

[30] Foreign Application Priority Data

Jan. 31, 1996 [JP] Japan .................................. 8-039012
Dec. 5, 1996 [JP] Japan .................................. 8-342633

[51] Int. Cl.[6] ............................................. G01N 27/26
[52] U.S. Cl. ...................................................... 204/429
[58] Field of Search ........................................... 204/429

[56] References Cited

U.S. PATENT DOCUMENTS

| | | | |
|---|---|---|---|
| 4,402,820 | 9/1983 | Sano et al. | 204/429 |
| 4,915,814 | 4/1990 | Harada et al. | 204/429 |
| 5,160,598 | 11/1992 | Sawada et al. | 204/429 |
| 5,310,575 | 5/1994 | Friese et al. | 204/429 |
| 5,443,711 | 8/1995 | Kojima et al. | 204/429 |
| 5,472,591 | 12/1995 | Saito et al. | 204/429 |
| 5,486,279 | 1/1996 | Friese et al. | 204/429 |
| 5,522,979 | 6/1996 | Tatumoto et al. | 204/429 |
| 5,593,558 | 1/1997 | Sugino et al. | 204/429 |

FOREIGN PATENT DOCUMENTS

| | | |
|---|---|---|
| 51-145390 | 12/1976 | Japan . |
| 1-227955 | 9/1989 | Japan . |
| 6174683 | 6/1994 | Japan . |

*Primary Examiner*—Bruce F. Bell
*Attorney, Agent, or Firm*—Cushman Darby & Cushman IP Group of Pillsbury Madison & Sutro LLP

[57] ABSTRACT

An oxygen concentration detecting device comprises a solid electrolyte body, inner and outer electrodes formed on the opposite sides of the solid electrolyte body, and a protective layer formed on the outer electrode and comprised of coarse particles and fine particles mutually bonded through an inorganic binder while substantially keeping the original forms of the both types of particles. A ratio of an average particle size, RB, of the coarse particles to an average particle size, RA, of the fine particles of 30:1 or above, and a content, WA, of the fine particles in the protective layer based on the total content, W, of the content, WA, of the fine particles and the content, WB, of the coarse particles on the weight basis is in the range of 15 to 80 %. A method for fabricating the detecting device having such a protective layer as set out above is also described.

20 Claims, 5 Drawing Sheets

OXYGEN CONCENTRATION DETECTING DEVICE AND METHOD FOR FABRICATING THE SAME

BACKGROUND OF THE INVENTION

1. Field of The Invention

This invention relates to an oxygen concentration detecting device which is useful in the control of combustion of internal combustion engines and also to a method for fabricating such a device as mentioned above.

2. Description of The Prior Art

For the detection of a concentration of oxygen in an exhaust gas from internal combustion engines of automotive vehicles, $ZrO_2$ solid electrolyte has been often employed in gas detectors. For instance, oxygen detectors of the oxygen concentration electromotive force type have been well known and, in fact, have been in wide use.

The oxygen detectors have an oxygen concentration detecting element or device therein. The oxygen concentration detecting device includes a solid electrolyte body made, for example, of an oxygen ion conductive metal oxide such as a $ZrO_2 \cdot Y_2O_3$ solid solution. An outer electrode is provided on an outer surface of the solid electrolyte body which is exposed to a gas to be measured. An inner electrode is provided on an inner surface of the body which is exposed to a reference gas. In general, the outer and inner electrodes are each made of a metal which serves as a kind of catalyst, e.g. Pt.

In order to protect the outer electrode, a porous protective layer through which the gas to be measured is able to pass is formed on the outer electrode. Such a protective layer is made, for example, of a heat-resistant metal oxide.

Figure 4:
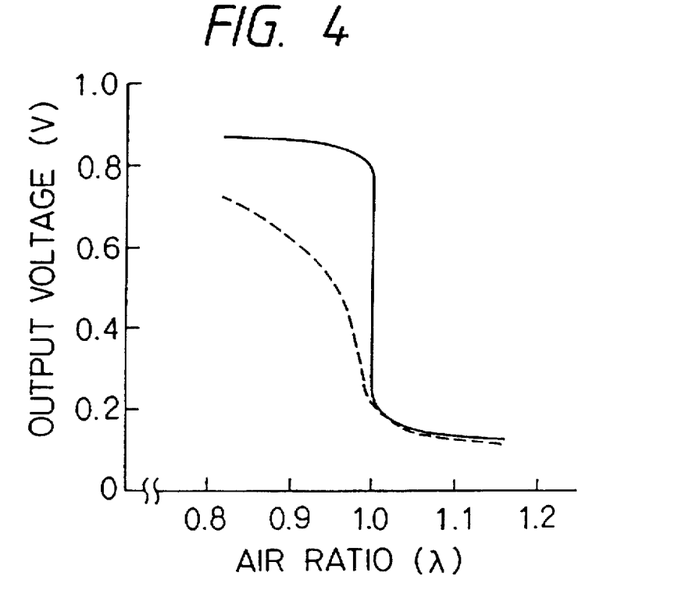
FIG. 4 is a graph showing the relation between the output voltage and the air ratio of the device.

For preventing non-combusted substances in an exhaust gas to be measured from deposition on the outer electrode and for promoting the equilibrium reactions of carbon monoxide and hydrocarbons contained in the exhaust gas with residual oxygen on the outer electrode, the protective layer of the detecting device should be arranged as having an appropriately dense structure. By this, a satisfactorily controlled passage of the gas to be measured is attained, thereby ensuring a sharp output characteristic as will be described in more detail with reference to FIG. 4. More particularly, the protective layer should have a porosity and an average pore size, both of which are appropriately small enough to appropriately control the passage of the gas to be measured.

In prior art, as set out in Japanese Laid-open Patent Application No. 51-145390, the protective layer is formed according to a plasma spray coating technique wherein the powder of a heat-resistant metal oxide such as spinel is plasma spray coated and deposited at high temperatures on the surface of the outer electrode.

However, the protective layer formed by the prior art method has the following problems.

The heat-resistant metal oxide is so high in melting point that a difficulty is involved in melting the oxide in a plasma flame. This makes it difficult to make a small pore size in the protective layer. Thus, there is the apprehension that the pores formed in the protective layer are relatively large, and a dense protective layer is unlikely to form. In order to obtain an appropriately controlled "gas passage-reducing effect" (i.e. a gas diffusion-resistant effect) while using such a protective layer as mentioned above, the protective layer has to be thick enough to attain the effect on the reduction.

In general, the plasma spray coating technique is one wherein a starting metal oxide is not efficiently utilized with a poor yield, and great electric power is required for the plasma spray coating. In addition, an apparatus for carrying out the technique undesirably has to be on a large scale, and much cost therefor is necessary.

Japanese Laid-open Patent Application No. 1-227955 has proposed an oxygen concentration detecting device which includes a protective layer. The protective layer is formed by initially forming a layer of coarse particles obtained by plasma spray coating and having a great porosity. The spaces or interstices in the coarse particle layer are filled with ultrafine particles by vacuum impregnation or by impregnation under pressure. The resulting protective layer has a small porosity.

In order to permit the spaces of the coarse particle layer to be substantially uniformly filled with the ultrafine particles, however, the average size of the ultrafine particles should be in the range of 0.01 to 0.5 μm. If ultrafine particles whose average particle size is smaller than 0.1 μm, there is the great possibility that the resultant protective layer is apt to suffer cracking on use.

As a matter of course, the vacuum impregnation or the impregnation under pressure needs additional specific operations and devices. In addition, it is difficult to reliably pack or fill the ultrafine particles in the spaces of the initially formed coarse particle layer, with a further difficulty in confirming that the spaces have been fully filled.

The layer of the coarse particles which is formed by plasma spray coating is so arranged that the coarse particles are mutually melt bonded together. In other words, the coarse particles become flat during the course of the melt bonding and act as a kind of aggregate for the protective layer. This means that in the protective layer, the coarse particles and the ultrafine particles locally differ in a mixed condition thereof, so that the composition of the protective layer may not be uniform throughout the layer. This results in the formation of the protective layer whose porosity locally varies, thereby causing an unstable output characteristic.

In general, an exhaust gas contains elemental components derived from oils such as P, Ca, Zn, Si and the like, and components derived from gasoline such as K, Na, Pb and the like (both components being hereinafter referred to simply as poisoning components). In known oxygen concentration detecting devices using a plasma spray-coated layer, a problem has been involved in that the poisoning components deposit on the surface of the detecting device to cause the protective layer to be clogged in the surfaces thereof. This worsens the output characteristic of the detecting device.

In order to prevent the clogging with the poisoning components, Japanese Laid-open Patent Application No. 6-174683 proposes the provision of a so-called trap layer on the surface of a protective layer. The trap layer is formed as a porous layer which is made, for example, of a heat-resistant metal oxide such as $\gamma\text{-}Al_2O_3$. The trap layer can prevent the poisoning but is inconvenient in that the oxygen concentration detecting device is complicated in structure along with the necessity of an additional fabrication step. This invites the problem that the fabrication cost increases.

SUMMARY OF THE INVENTION

It is accordingly an object of the invention to provide an oxygen concentration detecting device which overcomes the problems of the prior art counterparts and which includes a protective layer having a uniform porosity and a uniform average pore size while keeping controlled diffusion of a gas to be measured through the protective layer along with a good resistance to poisoning.

It is another object of the invention to provide an improved oxygen concentration detecting device which has a good output characteristic.

It is a further object of the invention to provide an oxygen concentration detecting device wherein a protective layer is formed by a specific manner whereby a more improved detecting device is obtained It is a further object of the invention to provide a method for fabricating an oxygen concentration detecting device which can effectively utilize starting materials for a protective layer thereof and which is simple in procedure and ensures easy and inexpensive fabrication of the detecting device.

According to a broad aspect of the invention, there is provided an oxygen concentration detecting device which comprises a solid electrolyte body, an inner electrode formed on an inner side of the solid electrolyte body and exposed to a reference gas fed from outside, an outer electrode formed on an outer side of the solid electrolyte body and exposed to a gas to be measured, and a protective layer formed on the outer electrode, wherein the protective layer has a structure which comprises coarse particles and fine particles packed in spaces formed among the coarse particles and the coarse particles and the fine particles are mutually bonded through a metal oxide derived from an inorganic binder while substantially keeping original forms of the coarse particles and the fine particles, a ratio of an average particle size, RB, of the coarse particles to an average particle size, RA, of the fine particles is such that the value of RB/RA is 30 or above, and a content, WA, of the fine particles in the protective layer based on the total, W, of the content, WA, of the fine particles and the content, WB, of the coarse particles on the weight basis is in the range of 15 to 80%.

When the value of RB/RA is defined to be 30 or above, the fine particles can be filled or packed satisfactorily in the spaces formed in the coarse particle layer. This leads to the formation of the protective layer which has a small porosity and a small average pore or void size sufficient for the purpose of the invention.

The upper limit of RB/RA should preferably be 500 or below, within which a dense protective layer can be stably obtained. The dense protective layer ensures a good effect of reducing a gas passage therethrough and is able to promote equilibrium reactions on the outer electrode. When the value of RB/RA exceeds 500, the deposition of the protective layer on the solid electrolyte body lowers, with the tendency toward the formation of cracks therein or the separation of the layer. The protective layer may not be densely formed.

According to a more specific and preferred embodiment of the invention, there is also provided an oxygen concentration detecting device of the type which comprises a solid electrolyte body, an inner electrode formed on an inner side of the solid electrolyte body and exposed to a reference gas fed from outside, an outer electrode formed on an outer side of the solid electrolyte body and exposed to a gas to be measured, and a protective layer formed on the outer electrode, wherein the protective layer has a structure which comprises coarse particles and fine particles packed in spaces formed among the coarse particles and wherein the coarse particles and the fine particles are mutually bonded through a metal oxide derived from an inorganic binder while substantially keeping original forms of the coarse particles and the fine particles, the protective layer being formed by a process which comprises depositing a slurry obtained by dispersing heat-resistant coarse particles and heat-resistant fine particles in a liquid medium therefor on the outer electrode, drying the deposited slurry, and baking the resultant layer, the layer having a ratio of an average particle size, RB, of the coarse particles to an average particle size, RA, of the fine particles of 30:1 or above provided that the value of RB/RA is 10 or above when the value of $(e \times d)/L$ is within a range of $2.0 \times 10^{-5}$ to $30 \times 10^{-5}$ wherein e, d and L are, respectively, a porosity, an average pore size by μm and a thickness by μm of the protective layer, and a content, WA, of the fine particles in the protective layer based on the total, W, of the content, WA, of the fine particles and the content, WB, of the coarse particles on the weight basis is in the range of 15 to 80%.

As will be apparent from the above, the protective layer is formed by a simple procedure which comprises depositing the slurry on the outer electrode, drying the slurry by heating to leave the particle layer, and baking the particle layer. The protective layer formed by this process makes full use of starting particulate materials and ensures a high yield of the materials and can be formed by a simple manner without use of any large-scale apparatus. In addition, this protective layer can be formed more inexpensively than one which is formed by plasma spray coating in prior art.

In the above process, the coarse particles and the fine particles can be uniformly mixed and dispersed in a liquid medium. These two types of particles can be uniformly deposited on the outer electrode, resulting in uniform porosity and average pore size in the protective layer. The two types of particles are strongly bonded together through a metal oxide derived from an inorganic binder mixed therewith while substantially keeping the original forms of the starting coarse and fine particles.

According to a further embodiment of the invention, there is provided a method for making an oxygen concentration detecting device of the type which comprises a solid electrolyte body, an inner electrode formed on an inner side of the solid electrolyte body and exposed to air fed from outside, an outer electrode formed on an outer side of the solid electrolyte body and exposed to a gas to be measured, and a protective layer formed on the outer electrode, wherein the protective layer has a structure which consists of coarse particles and fine particles packed in spaces formed among the coarse particles, the method comprising applying or depositing, on the outer electrode, a slurry obtained by dispersing heat-resistant coarse particles and fine particles in a liquid medium, drying the thus applied slurry, and baking the resultant layer whereby the protective layer has such a structure wherein the coarse particles and the fine particles are mutually bonded through a metal oxide derived from an inorganic binder while substantially keeping original forms of the coarse particles and the fine particles.

PREFERRED EMBODIMENTS OF THE INVENTION

Reference is now made to the accompanying drawings and particularly, to FIGS. 1 to 4. In the accompanying drawings, like reference numerals indicate like parts or members unless otherwise indicated.

Figure 1:
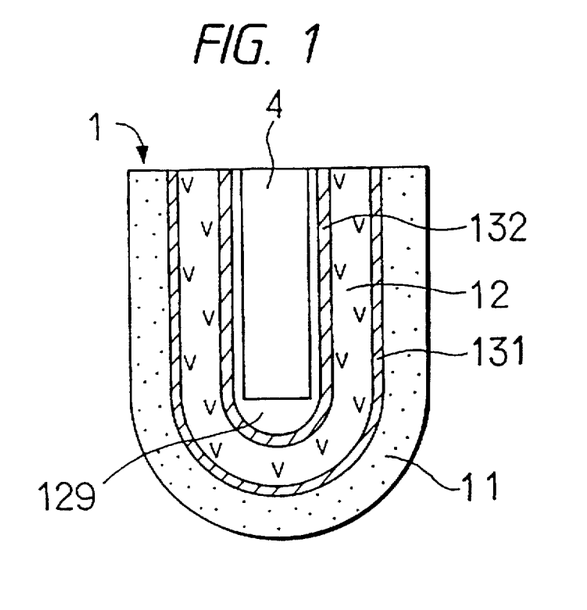
FIG. 1 is a schematic sectional view of an oxygen concentration detecting device according to one embodiment of the invention.

An oxygen concentration detecting device generally indicated at 1 in FIG. 1 is of the oxygen concentration electromotive force type. As shown in FIG. 1, the oxygen concentration detecting device 1 is in the form of a U shape in section and includes a U-shaped solid electrolyte body 12 having an inner electrode 132 on the inner surface of the body 12 and an outer electrode 131 on the outer surface of the body 12.

Figure 2:
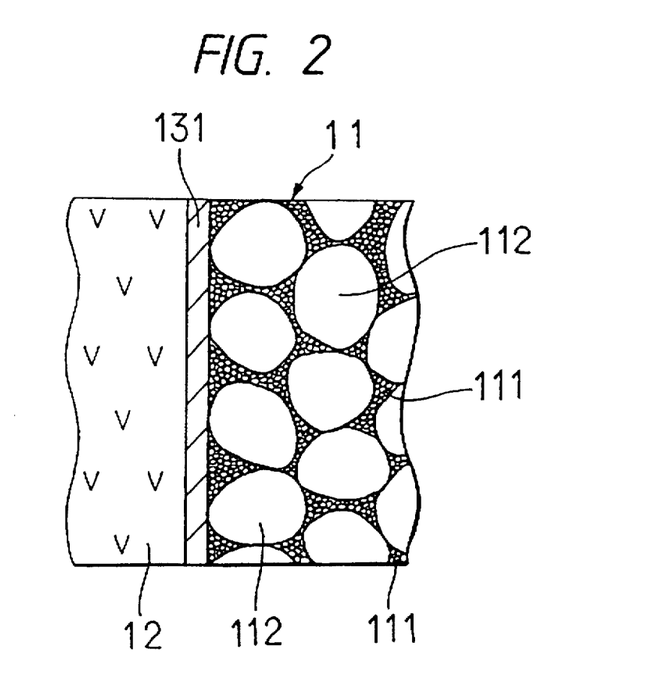
FIG. 2 is an enlarge sectional view showing part of a protective layer of the device of FIG. 1.

A protective layer 11 is further formed on the outer electrode 131. As shown in FIG. 2, the protective layer 11 consists of coarse particles 112 and fine particles 111 and has such a structure wherein the fine particles are packed in spaces formed among the coarse particles 112 as shown. These particles are bonded together through a metal oxide (not shown) derived from an inorganic binder.

In FIG. 1, a heater 4 is placed in a chamber 129 into which air is introduced as a reference gas when the device 1 is in operation. The heater 4 is used to heat the device 1 to an activation temperature.

The solid electrolyte body 1 may be made of any solid electrolytes ordinarily used for this purpose, including mixtures of $ZrO_2$ and $Y_2O_3$, and the like. The solid electrolyte body may be shaped, for example, in the form of a cup closing at one end and opening at the other end as shown in FIG. 1 although other forms may also be used provided that the chamber 129 is formed for a reference gas.

The inner and outer electrodes 132, 131 may be, respectively, made of a metal such as Pt, Rh or the like as usual.

As defined hereinbefore, the protective layer 11 should consist of the fine particles 111 and the coarse particles 112 wherein when an average particle size of the fine particles 111 is taken as RA and an average size of the coarse particles 112 is takes as RB, the value of RB/RA is 30 or above. In this range of the value of RB/RA, the spaces formed among the coarse particles 112 can be satisfactorily filled with the fine particles 111 as shown in FIG. 2. Thus, the protective layer 11 has a porosity and an average pore size which are small and uniform enough to provide a good output characteristic.

When the device having such a protective layer on the outer electrode is exposed to an exhaust gas from internal combustion engines as a gas to be measured, the protective layer permits an appropriately controlled gas passage therethrough in order to accelerate equilibrium reactions of carbon monoxide and hydrocarbons with residual oxygen contained in the gas to be measured on the outer electrode. The term "appropriately controlled gas passage" is intended to mean that a well controlled resistance to the diffusion of a gas to be measured through the protective layer is imparted to the protective layer, and may be sometimes called a gas passage-reducing effect or the like hereinafter.

The average particle size, RA, of the fine particles used in the protective layer should preferably be in the range of 0.1 µm to less than 1 µm. If the value of RA is less than 0.1, the protective layer is liable to crack when dried during the course of the formation thereof. If cracking takes place in the protective layer, a porosity and an average pore size increase correspondingly to the size and the number of cracks. An appropriately controlled gas passage through the protective layer may not be attained.

On the other hand, when the value of RA exceeds 1 µm, the spaces of the coarse particles may not be satisfactorily filled with the fine particles, resulting in the formation of the layer having undesirably great porosity and average pore size.

The average particle size, RB, of the coarse particles should be greater than the average particle size, RA, and is preferably in the range of 3 to 50 µm.

If the value of RB is smaller than 3 µm, the fine particles may not be appropriately filled in the spaces formed by the coarse particles. This leads to too great a porosity and an average pore size in the protective layer.

On the other hand, when the value of RB exceeds 50 µm, the bonding force of the coarse particles may lower when the protective layer is baked against the outer electrode. This may result in the separation of the protective layer from the outer electrode when the detecting device is in use.

The size distribution of the fine particles should preferably be such that particles having a particle size of 0.5×RA to 3×RA wherein RA is an average particle size are contained in amounts of at least 80% based on the total of the fine particles. Likewise, the coarse particles should preferably have such a size distribution that particles having a particle size of 0.5×RB to 3×RB wherein RB is an average particle size are contained in amounts of at least 80% based on the total of the coarse particles.

If the size distributions are, respectively, outside the above ranges and are each in a broad fashion, the size of the spaces formed by the coarse particles becomes greatly varied. Moreover, the size of the fine particles filled in individual spaces also becomes varied. As a whole, the porosity and the average pore size in the protective layer may undesirably become great.

The ratio between the content, WA, of the fine particles in the protective layer and the total, W, of the content, WA, of the fine particles and the content, WB, of the coarse particles (i.e. W=WA+WB) should be 15 to 80:100, preferably 15 to 60:100.

If the ratio is in the above-defined range, the fine particles are satisfactorily filled in the spaces of the coarse particles as shown in FIG. 2, ensuring appropriately controlled small porosity and average pore size in the protective layer.

If the value of WA/W is less than 15/100, the fine particles become so short in amount that the spaces created by the coarse particles may not be filled well with the fine particles. Thus, the porosity and the average pore size in the protective layer may not be reduced as intended.

On the other hand, when the value of WA/W is greater than 80/100, the volume of the fine particles becomes greater than the volume of the spaces of the coarse particles. In this condition, the protective layer is occupied by a majority of the fine particles while leaving the coarse particles as a kind of islands. In this case, the porosity and the average pore size in the protective layer become non-uniform, disenabling one to attain an appropriately controlled gas passage through the protective layer.

It should be noted that the contents, WA, WB and W are by weight.

The coarse particles and the fine particles used in the protective layer should preferably be made of at least one heat-resistant material selected from $Al_2O_3$, $ZrO_2$, $MgO \cdot Al_2O_3$ spinel, and mullite.

The heat-resistant particles are thermally, chemically stable, so that the protective layer is very unlikely to degrade when the device is in practical application, and keeps its stable characteristics. This becomes more pronounced when the device is exposed to high temperature atmospheric conditions.

The coarse particles and the fine particles may be in any forms such as, for example, spheres, blocks, plates, columns, needles and the like.

The thickness of the protective layer should preferably be in the range of from 100 to 300 µm in order to attain a good porosity and a good average pore size although depending on the mixing ratio between the coarse and fine particles.

Figure 3:
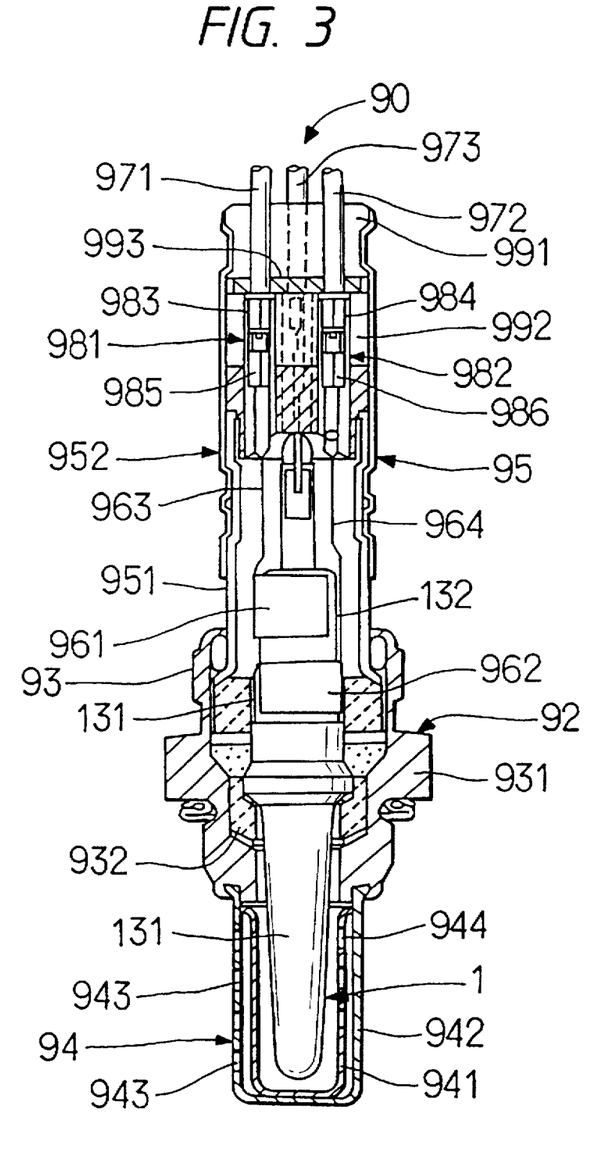
FIG. 3 is a schematic sectional view of an oxygen detector to which the device of the invention is applied.

In practice, the oxygen concentration detecting device 1 is usually set in position of an oxygen detector 90 shown, for example, in FIG. 3. The detector 90 is set in an exhaust gas passage of an automotive engine in order to control the combustion thereof.

The detector 90 includes an oxygen concentration detecting device 1 and a housing 92 accommodating the device 1 therein. The housing 92 has a trunk portion 93 provided with a flange substantially at the center thereof, and also has, below the trunk portion 93, an exhaust gas cover 94 which is inserted into an exhaust gas passage. An air cover 95 is provided above the trunk 93.

The exhaust gas cover 94 has an inner cover 941 and an outer cover 942, both made of a stainless steel. The inner cover 941 and the outer cover 942 are, respectively, provided with exhaust gas inlets 944, 943.

The space partitioned with the inner cover 941 is a chamber for a gas to be measured in the detector 90.

The air cover 95 has a main cover 951 attached to the trunk portion 93 and a sub-cover 952 covering the upper portion of the main cover 951. The main cover 951 and the sub-cover 952 are, respectively, provided with air (i.e. a reference gas) inlets not shown in the figure.

The air introduced from the respective air inlets is introduced via the air cover 95 into the air chamber 129 of the detecting device 1 shown in FIG. 1.

The detecting device 1 is held through an insulating member 932 in the inside of the trunk portion 93 as shown. The outer electrode 131 and the inner electrode 132 of the detecting device 1 are, respectively, connected with metallic plate terminals 961, 962 held to surround the electrodes therewith.

The plate terminals 961, 962 are, respectively, connected to lead wires 971, 972. More particularly, the plate terminals 961, 962, respectively, have elongated terminal pieces 963, 964. The terminal pieces 963, 964 are connected to ends 985, 986 of connectors 981, 982 to which the lead wires 971, 972 are connected, respectively.

The plate terminals 961, 962 are each made of a metallic plate of an inverted T form which is shaped in the form of a cylinder and hold the inner electrode 132 and the outer electrode 131 therewith. The plate terminals 961, 962 are urged to contact, under pressure, with the inner electrode 132 and the outer electrode 131 owing to the spring action of the metallic plates.

The lead wires 971, 972 are exerted with a pull force along the axial direction of the oxygen detector 90, so that the plate terminals 961, 962 are pulled via the connectors 981, 982 and, thus, may slide along the axial direction. In order to prevent the sliding, the detector 90 is provided with a stopper 993 intervening between rubber bushes 991, 992.

The stopper 993 is to suppress the movement of the connector 981, 982 and is made of a resin material for keeping the insulation between the lead wires 971, 972.

In FIG. 3, reference numeral 973 indicates a wire for the heater 4 for heating the detecting device 1.

The detector 90 is fixed in an exhaust gas passage by inserting the exhaust gas cover 94 into the gas passage and fixing with the flange 931.

As stated hereinbefore with reference to FIG. 2, the protective layer 11 of the detecting device 1 has a structure wherein the fine particles 111 are filled in the spaces of the coarse particles 112 in a manner as defined hereinbefore. By the structure, the porosity and the average pore size in the protective layer 11 are, respectively, small and uniform. Preferably, the porosity is in the range of 50% or below and the average pore size is in the range of 0.01 to 0.3 µm when determined by use of a mercury porosimeter.

Especially, when an exhaust gas from automotive engines is used as a gas to be measured, the protective layer 11 can appropriately control the passage of the gas therethrough, so that the equilibrium reactions of carbon monoxide and hydrocarbons with residual oxygen in the gas to be measured are accelerated. When using the detecting device of the invention, a sharp output characteristic shown by the solid line in FIG. 4 can be obtained.

In a more specific embodiment of the invention, the detecting device 1 is fabricated by the process as defined hereinbefore. This process is described in more detail.

Initially, a solid electrolyte body 12 having a U shape in section is obtained by molding. More particularly, predetermined amounts of starting metal oxides such as $ZrO_2$ and $Y_2O_3$ are mixed, powdered and granulated by a usual manner. The granules are molded in a desired form and ground to obtain a molding. The thus obtained molding is sintered at a high temperature for several hours to obtain a solid electrolyte body 12 as shown in FIG. 1. The inner surface and the outer surface of the body 12 are made irregular such as by etching and then chemically plated to form an inner electrode 132 and an outer electrode 131.

The protective layer 11 is formed by providing two types of particles, i.e. coarse particles and fine particles, in predetermined amounts, mixing these particles, and dispersing the mixture in a liquid medium such as water to provide a slurry. Usually, an inorganic binder is added to the slurry. Preferably, the liquid medium is added to the mixed particles in an amount of from 10 to 50% by weight based on the mixed particles. Likewise, the inorganic binder is added in an amount of 1 to 10 wt % of the mixed particles. Examples of the inorganic binder include $Al(OH)_3$, $Si(OH)_4$, and the like. The addition of the inorganic binder permits mutual bonding of the particles and bonding of the protective layer to the outer electrode 131.

When the amount of the inorganic binder is less than 1%, the bonding force may not be satisfactory. On the other hand, when the amount exceeds 10%, there is the possibility that the protective layer is liable to crack.

The slurry is deposited on or applied onto the outer electrode 131 by spraying or dipping, preferably by dipping, followed by drying and baking at a temperature ranging from 500° to 1000° C. to form the protective layer 11 as shown in FIG. 1.

As will be apparent from the above process, the slurry comprising two types of the particles is deposited on the outer electrode, for example, by dipping, dried and sintered. The original forms of these particles are substantially maintained in the resulting protective layer, unlike the case of plasma spray coating wherein particles are semi-melted and thus deformed as flat.

In the fabrication method of the invention, the protective layer can be formed by a simple procedure which comprises depositing the slurry on the outer electrode, drying and baking the thus coated slurry.

This procedure makes full use of starting particles and provides a good yield of the particles. In addition, any large-scale equipment is not necessary. In other words, the oxygen concentration detecting device can be fabricated inexpensively and readily.

In the device obtained by the process, the coarse particles and the fine particles are uniformly mixed and dispersed in the slurry. This permits both types of particles to be uniformly coated on the outer electrode. The resultant protective layer has uniform porosity and average pore size.

The protective layer should have a ratio between the average particle size, RB, of the coarse particles and the average particle size, RA, (i.e. RB/RA) of 30:1 or above.

If the above requirement for the ratio is satisfied, the spaces of the coarse particles are satisfactorily filled with the fine particles. The protective layer has a porosity and an average size which are small enough for the controlled gas passage.

Alternatively, the protective layer should be such that the value of RB/RA is 10 or above provided that when the porosity, the average pore size and the thickness of the protective layer are, respectively, taken as $\epsilon$, d ($\mu$m) and L ($\mu$m), the value of ($\epsilon \times d$)/L is within a range of $2.0 \times 10^{-5}$ to $30 \times 10^{-5}$.

In this case, similar results are obtained with respect to the porosity and the average particle size.

If the value of RB/RA is less than 10, it may not possible to fully fill the spaces of the coarse particles with the fine particles, the resultant protective layer has a porosity and an average pore size greater than those defined before.

The upper limit of RB/RA should preferably be 500 or below. If the value of RB/RA exceeds 500, the deposition or bonding force of the protective layer may lower, resulting in cracking and separation of the layer. In addition, a dense layer may not be obtained, not permitting an appropriately controlled gas passage through the layer.

When the value of ($\epsilon \times d$)/L is less than $2.0 \times 10^{-5}$, the gas passage through the resultant protective layer can be appropriately controlled, so that the equilibrium reactions of carbon monoxide and hydrocarbons with residual oxygen in an exhaust gas proceed satisfactorily on the outer electrode to obtain a sharp output characteristic. However, the diffusion of the reactant gases may become so slow that the response delays. On the other hand, where the value exceeds $30 \times 10^{-5}$, the effect of reducing the gas passage is not so good that carbon monoxide, hydrocarbons and residual oxygen are not satisfactorily equilibrated. Thus, a sharp output characteristic is not attainable.

The porosity, $\epsilon$, of the protective layer should preferably be in the range of 50% or below. If the porosity is greater than 50%, a dense protective layer may not be obtained. Thus, the gas passage may not be reduced as controlled.

The average pore size, d, of the protective layer should preferably be within a range of 0.01 to 0.3 $\mu$m for the reason set out with respect to the definition of the porosity. When the average pore size, d, is less than 0.01, cracks may be produced at the time of drying the slurry to form the protective layer. An appropriately controlled gas passage may not be attained.

It is more preferred from the standpoint of preventing poisoning that the porosity, $\epsilon$, is in the range of 15%<$\epsilon$<50% and the value of ($\epsilon \times d$) is in the range of $5.0 \times 10^{-3}$ to $40 \times 10^{-3}$.

As stated in the "Description of the Prior Art", the protective layer of the oxygen concentration detecting device should have a porosity and an average pore size, both of which are appropriately small in order to prevent non-combusted substances in an exhaust gas to be measured from deposition of the outer electrode, and to appropriately control a gas passage through the protective layer thereby promoting equilibrium reactions of carbon monoxide, hydrocarbons and residual oxygen in the exhaust gas on the outer electrode to obtain a sharp output characteristic.

Where a gas to be measured, which contains large amounts of poisoning components, is subjected to measurement using a known oxygen concentration detecting device having a protective layer formed by plasma spraying, the poisoning components are very liable to deposit on the surface of the detecting device. This causes the protective layer to be clogged in the surfaces thereof. Eventually, the output characteristic of the detecting device is degraded by poisoning.

It has been found that when the porosity, $\epsilon$, and the value of ($\epsilon \times d$) are, respectively, defined within the above ranges, the gas passage can be appropriately reduced and the clogging in the surfaces of the protective layer can be prevented. Thus, a good resistance to poisoning is imparted to the protective layer.

If the value of ($\epsilon \times d$) is less than $5.0 \times 10^{-3}$, a gas diffusion may be reduced to a satisfactory extent but the protective layer becomes so dense that poisoning components contained in an exhaust gas deposit on and in the surfaces of the protective layer, thereby causing the layer to be readily clogged. On the other hand, when the above value exceeds $40 \times 10^{-3}$, such a protective layer which has a defined range of ($\epsilon \times d$)/L cannot be formed from the standpoint of the layer thickness.

In the protective layer, a ratio between the content, WA, of the fine particles and the total, W, of the content, WA, of the fine particles and the content, WB, of the coarse particles (i.e. W=WA+WB) is preferably in the range of 15 to 80:100. Within this range, the fine particles are filled in the spaces of the coarse particles, resulting in a small porosity and a small average pore size in the protective layer.

In the process of forming the protective layer, the slurry is dried after the deposition. The drying is preferably carried out at a temperature ranging from 15° to 25° C. for 60 to 120 minutes.

Thereafter, the resultant layer is preferably baked at a temperature of 500° to 1000° C. for about 1 hour to obtain a protective layer having strong bonding and deposition forces.

If the baking temperature is lower than 500° C., the inorganic binder may not satisfactorily act to bond the particles mutually and bond the layer to the solid electrolyte body. On the other hand, when the baking temperature is higher than 1000° C., the coarse and fine particles suffer shrinkage by sintering, with the possibility that the protective layer is cracked.

As will be apparent from the above, the coarse and fine particles are deposited from a slurry, dried and sintered under relatively mild conditions, so that the original forms of both particles are unlikely to deform. A protective layer having intended porosity and average pore size can be readily formed by a simple procedure.

Needless to say, preferred aspects of the detecting device obtained by the fabrication method which have been set out hereinabove are true of the fabrication method.

The fabrication method according to a further embodiment of the invention is substantially descried with reference to the detecting device fabricated by the process having set out hereinabove and is not repeated herein. In the method of the invention, the slurry may be deposited on the outer electrode by dipping, spraying, coating or the like.

Figure 5:
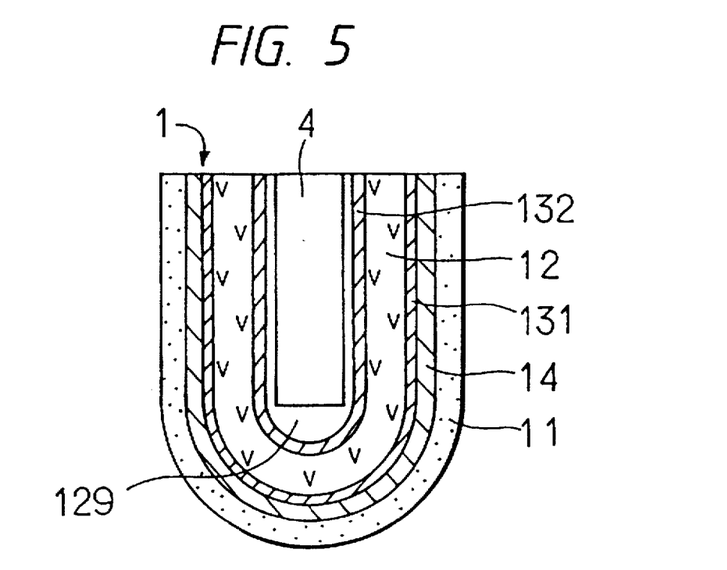
FIG. 5 is a schematic sectional view of an oxygen concentration detecting device according to another embodiment of the invention wherein a spray coated layer is included in the device.

Reference is now made to another embodiment of the invention shown in FIG. 5. The device 1 of FIG. 5 is similar to that of FIG. 1 except that a plasma spray coated layer 14 is formed directly on the outer electrode 131 and the protective layer 11 is further formed on the plasma spray coated layer 14.

The reason why the plasma spray coated layer 14 is formed on the outer electrode is that the bonding force between the outer electrode 131 and the layer 14 becomes stronger. When the resulting detecting device is employed under high ambient temperature conditions, the outer electrode is suppressed from degradation owing to the thermal cohesion. The layer 14 should preferably be formed in a thickness of from 30 to 100 μm. If the thickness is less than 30 μm, the degradation of the outer electrode by the thermal cohesion may not be prevented, under which when the detecting device is used under high temperature conditions, its output characteristic may lower. On the other hand, when the thickness exceeds 100 μm, the starting material cannot be effectively utilized owing to the poor yield of the plasma spray coating technique, thus increasing the fabrication cost.

The layer 14 is preferably made of heat-resistant metal oxides such as γ-$Al_2O_3$, α-$Al_2O_3$, MgO·$Al_2O_3$ spinel and the like. The heat-resistant metal oxides should preferably be in the form of particles having a size ranging from 10 to 80 μm prior to the plasma spray coating.

Figure 6:
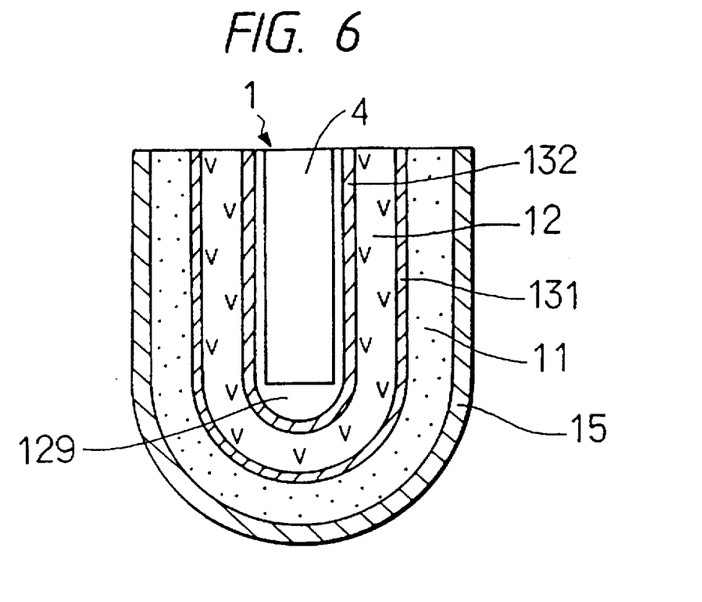
FIG. 6 is a schematic sectional view of an oxygen concentration detecting device according to a further embodiment of the invention wherein a trap layer is included in the device.

FIG. 6 shows another embodiment of the invention wherein a detecting device is similar to that of FIG. 1 except that a trap layer 15 is formed on the protective layer 11.

The trap layer 15 may be formed by mixing thermally stable ceramic particles such as of a-alumina, mullite, γ-$Al_2O_3$, MgO·$Al_2O_3$ spinel and the like, an inorganic binder such as alumina sol and a liquid medium such as water to obtain a slurry. The slurry is dipped or sprayed on the protective layer, followed by thermal treatment. The thermal treating conditions are those similar to those used for the formation of the protective layer. In order not to permit the trap layer 15 to impede the function of the protective layer 11, the layer 15 should preferably have a thickness of 10 to 500 μm. The trap layer 15 is effective in preventing poisoning with elemental components from oil components such as P, Ca, Zn, Si and the like and also those components from gasoline such as K, Na, Pb and the like.

Figure 7:
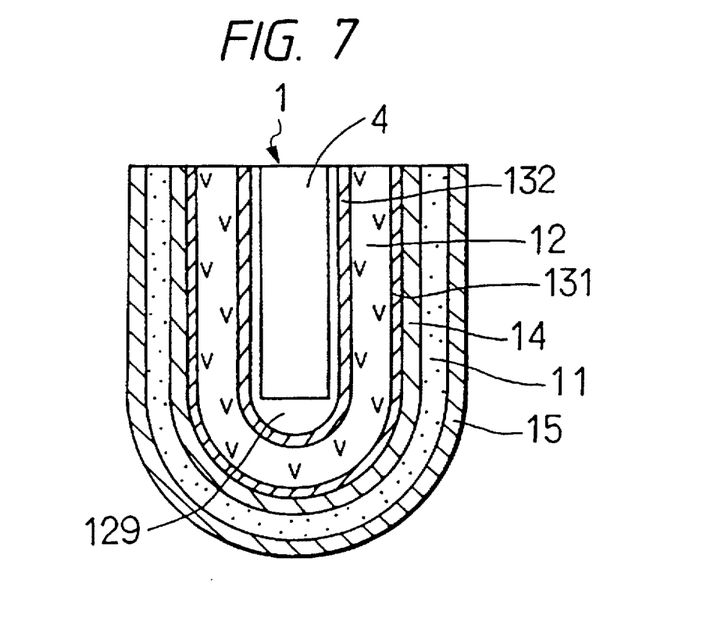
FIG. 7 is a schematic sectional view of an oxygen concentration detecting device according to a still further embodiment of the invention wherein both a spray-coated layer and a trap layer are included in the device.

FIG. 7 shows still another embodiment of the invention wherein a detecting device is similar to that of FIG. 1 except that a plasma spray coated layer 14 is formed on the outer electrode 131 and a trap layer 15 is formed on the protective layer 11. More particularly, the plasma spray coated layer 14 and the trap layer 15 as illustrated with reference to FIGS. 5 and 6 are both formed in the device 1.

In the foregoing embodiments, the device has a U-shaped section. The detecting device of the invention is not limited to those devices having U-shaped section.

Figure 8:
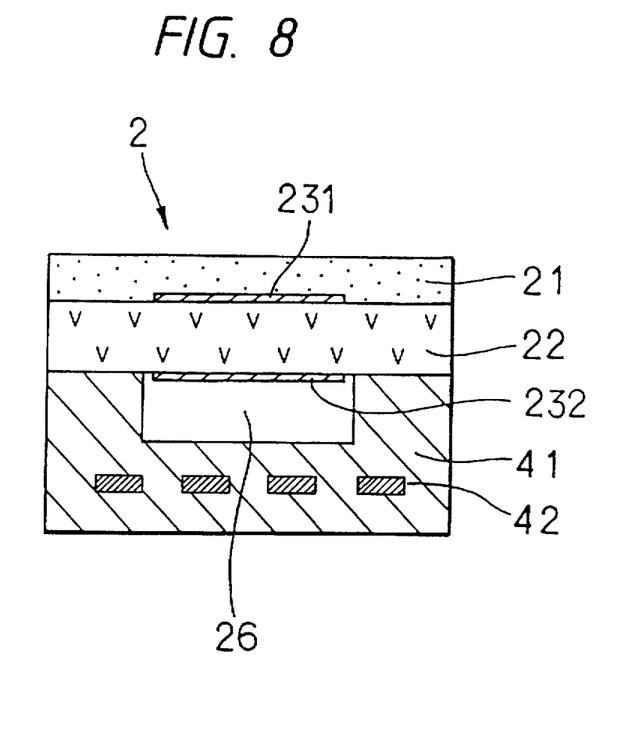
FIG. 8 is a schematic section view of an oxygen concentration detected device according to another embodiment of the invention.

FIG. 8 shows still another embodiment of the invention which includes an oxygen concentration detecting device 2 of a stacked type. The device 2 includes a plate-shaped solid electrolyte body 22, an outer electrode 231 and an inner electrode 232 formed on the outer and inner surfaces of the solid electrolyte body 22, respectively. The outer electrode 231 is exposed in a chamber of a gas to be measured in a manner as shown in FIG. 3. A protective layer 21 is formed over the outer electrode 231 as shown.

A heater 41 is provided on the inner surface of the solid electrolyte body 22 and has heating elements 42 built therein. The heater 41 is made of $Al_2O_3$ and the like ceramics. The heater 41 is so shaped as having a duct 26 in which the inner electrode 232 is exposed. This duct serves as a chamber for a reference gas such as air.

The protective layer 21 may be likewise formed as in the foregoing embodiments. The heater having built-in heating elements is well known in the art and its fabrication is not set out herein.

All the fabrication conditions and parameters for the protective layer as defined in the foregoing embodiments are also applicable to this embodiment. This type of detecting device has similar effects as those devices having a U-shaped section.

The invention is more particularly described by way of examples.

EXAMPLE 1

In this example, an oxygen concentration detecting device of the type shown in FIG. 1 was fabricated.

A cup-shaped solid electrolyte body which was closed at one end and opened at the other end (i.e. a U-shaped section) was molded. More particularly, 95 mole % of $ZrO_2$ and 5 mole % of $Y_2O_3$ were mixed and pulverized, followed by granulation by use of a spray dryer to provide starting granules.

The granules were molded into a desired cup shape and ground as desired to obtain a green molding. The green molding was sintered at 1600° C. for 2 hours. In this manner, a solid electrolyte body 12 of FIG. 1 was obtained.

The body 12 was made irregular on inner and outer surfaces thereof by etching, followed by chemical plating to form an inner electrode 132 and an outer electrode 131, both having a thickness of 1 μm.

$Al_2O_3$ was provided as heat-resistant particles, from which coarse particles 112 and fine particles were made. The average particle sizes RA, RB and a value of WA/JW of the fine particles 111 and the coarse particles 112 are indicated in Table 1.

The coarse and fine particles 112, 111 were mixed to obtain a mixture. 20 parts by weight of water and 2 parts by weight of Al(OH)$_3$ serving as an inorganic binder were added to 100 parts by weight of the mixture to obtain a slurry.

The slurry was applied onto the surface of the outer electrode 131 by dipping. The thus applied solid electrolyte body 12 was dried, heated and baked at 700° C. to form a protective layer 11 having a porosity and an average pore size indicated in Table 1.

The above procedure was repeated thereby obtaining oxygen concentration detecting devices of sample Nos. 1 to 18 which, respectively, had different particle sizes RA and RB of the fine particles and the coarse particles, different values of RB/RA, different mixing ratios of WA to W and different thicknesses of the protective layer. These are shown in Table 1.

For reference, the above procedure was repeated except that the protective layer was formed by plasma spray coating to provide a device of sample No. 19.

The performance of these samples was evaluated by setting each sample in an oxygen detector shown in FIG. 3 to determine the relation between the output voltage and the air ratio, γ. An oxygen concentration detecting device which had good capability of gas passage control exhibited such a relation as shown by the solid line in the figure. More particularly, the output voltage abruptly varied in the vicinity of γ=1 wherein the difference between the output voltage at the rich side and the output voltage at the lean side is great.

On the other hand, a device whose capability of gas passage control was poor had the relation as shown in the broken line in FIG. 3. That is, the variation of the output voltage varied gently in the vicinity of γ=1, i.e. the difference between the output voltages at rich and lean sides is small.

Each of the sample Nos. 1 to 19 was set in position of an exhaust pipe of an automotive engine. The air ratio was gradually varied while measuring an output voltage of the sample. More particularly, the air ratio, γ, was change from 0.9 to 1.1 to measure the output voltage of each detecting device. The results are shown in Table 1. A detecting device was evaluated as excellent the difference between the output voltages during the measurement was or above, as good for a difference ranging from 0.5 to less than 0.6 V, and bad for a difference ranging less than 0.5 V.

EXAMPLE 2

The oxygen concentration detecting device of the type shown in FIG. 5 was fabricated substantially in the same manner as in Example 1 except that after the formation of the inner electrode 132 and the outer electrode 131 on the opposite sides of the solid electrolyte body 12, a plasma spray coated layer 14 made of $MgO \cdot Al_2O_3$ spinel was formed on the outer electrode 131, followed by further formation of the protective layer 11.

In this manner, the detecting devices of sample Nos. 20 to 30 were made wherein these samples were made as having different thicknesses of the spray coated layer, porosities, average pore sizes, particles sizes RA and RB of the fine and coarse particles, values of RB/RA and contents of the fine particles relative to the total content of both types of particles, WA(W, and thicknesses of the protective layer shown in Table 2.

The sample Nos. 20 and 30 are for comparison, which did not have any spray coated layer. The sample Nos. 28 to 30 had any protective layer therein.

Each sample device was tested in the same manner as in Example 1 to evaluate the effect on the gas passage reduction, with the results shown in Table 2.

Further, the heat resistance was evaluated according to the following accelerated durability test. Each sample device was placed in an electric furnace wherein it was heated at a temperature of 1000° C. for 100 hours. When the area of the

TABLE 1

| | | | | | | Protective Layer | Gas Passage Reducing Effect | |
| | | | | | | Average | | |
| Sample No. | RA (μm) | RB (μm) | RB/RA | WA/W (%) | Porosity (%) | pore size (μm) | Thickness 100 μm | Thickness 200 μm |
| --- | --- | --- | --- | --- | --- | --- | --- | --- |
| 1 | 1 | 10 | 10 | 30 | 30 | 0.30 | bad | bad |
| 2 | 0.5 | 10 | 20 | 30 | 26 | 0.15 | bad | good |
| 3 | 0.3 | 10 | 33 | 20 | 24 | 0.11 | good | excellent |
| 4 | 0.3 | 10 | 33 | 30 | 22 | 0.09 | good | excellent |
| 5 | 0.3 | 10 | 33 | 40 | 25 | 0.10 | good | excellent |
| 6 | — | 10 | — | 0 | 46 | 3.00 | bad | bad |
| 7 | 0.2 | 10 | 50 | 10 | 30 | 0.34 | bad | bad |
| 8 | 0.2 | 10 | 50 | 15 | 25 | 0.10 | good | excellent |
| 9 | 0.2 | 10 | 50 | 20 | 22 | 0.05 | excellent | excellent |
| 10 | 0.2 | 10 | 50 | 30 | 18 | 0.04 | excellent | excellent |
| 11 | 0.2 | 10 | 50 | 40 | 23 | 0.05 | excellent | excellent |
| 12 | 0.1 | 10 | 100 | 20 | 22 | 0.04 | excellent | excellent |
| 13 | 0.1 | 10 | 100 | 30 | 19 | 0.04 | excellent | excellent |
| 14 | 0.1 | 10 | 100 | 40 | 23 | 0.04 | excellent | excellent |
| 15 | 0.1 | 5 | 50 | 30 | 19 | 0.04 | excellent | excellent |
| 16 | 0.1 | 3 | 30 | 20 | 26 | 0.08 | good | excellent |
| 17 | 0.1 | 3 | 30 | 30 | 23 | 0.06 | good | excellent |
| 18 | 0.4 | 20 | 50 | 30 | 20 | 0.12 | good | excellent |
| 19 | plasma spray coating | | | | 10 | 0.15 | good | excellent |

The results of the above Table reveal that the samples Nos. 3 to 5 and 8 to 18 which are those of the present invention exhibit the good effect on the reduction substantially equal to or better than the sample No. 19 including the protective layer formed by the plasma spray coating.

Especially, with the sample Nos. 9 to 15, the porosity and the average pore size are very small, so that an excellent effect on the gas passage reduction is attained even when the thickness of the protective layer is small.

The sample Nos. 1, 2, 6 and 7 which are outside the scope of the invention with respect to the content of the fine particles are poor in the effect on the reduction.

pores formed by thermal cohesion in the outer electrode was 30% or above based, on the total area of the outer electrode, such a sample was evaluated as bad. Likewise, a sample was evaluated as good when the area relative to the total area was in the range of 10 to less than 30%, and as excellent when the area was less 10%.

TABLE 2

| Sample No. | Plasma Spray Coated Layer | | | Protective Layer | | | | | | | Effect of Reduction | Heat Resistance |
|---|---|---|---|---|---|---|---|---|---|---|---|---|
| | Thickness (μm) | Porosity (%) | Average Pore Size (μm) | Thickness (μm) | RA (μm) | RB (μm) | RB/RA | WA/W (%) | Porosity (%) | Average Pore Size (μm) | | |
| 20 | — | — | — | 200 | 0.2 | 10 | 50 | 30 | 18 | 0.04 | excellent | good |
| 21 | 10 | 10 | 0.15 | 200 | 0.2 | 10 | 50 | 30 | 18 | 0.04 | " | good |
| 22 | 30 | 10 | 0.15 | 150 | 0.2 | 10 | 50 | 30 | 18 | 0.04 | " | excellent |
| 23 | 30 | 10 | 0.15 | 100 | 0.2 | 10 | 50 | 30 | 18 | 0.04 | " | " |
| 24 | 50 | 10 | 0.15 | 100 | 0.2 | 10 | 50 | 30 | 18 | 0.04 | " | " |
| 25 | 50 | 10 | 0.15 | 50 | 0.2 | 10 | 50 | 30 | 18 | 0.04 | " | " |
| 26 | 50 | 10 | 0.15 | 100 | 0.3 | 10 | 33 | 30 | 22 | 0.09 | " | " |
| 27 | 50 | 10 | 0.15 | 100 | 0.3 | 10 | 33 | 20 | 24 | 0.11 | " | " |
| 28 | 100 | 10 | 0.15 | 0 | — | — | — | — | — | — | good | " |
| 29 | 200 | 10 | 0.15 | 0 | — | — | — | — | — | — | excellent | " |
| 30 | 0 | — | — | 0 | — | — | — | — | — | — | bad | bad |

As will be apparent from Table 2, the sample Nos. 22 to 27 according to a preferred embodiment of the invention having the plasma spray coated layer exhibited an excellent effect on the reduction and an excellent heat resistance.

The sample Nos. 20, 21 which had no plasma spray coated layer or a thin plasma spray coated layer are inferior in the heat resistance to the sample Nos. 22 to 27.

The sample Nos. 28, 29 which had very thick plasma spray coated layers are excellent in the heat resistance along with a certain effect on the gas passage reduction because the spray coated layer serves also as a kind of protective layer. However, where the plasma spray coated layer is made thick, the yield of the starting material is poor and thus, the starting material cannot be utilized effectively. In addition, it is difficult to provide stable performance.

The sample No. 30 has neither any spray coated layer nor any protective layer, resulting in the poor effect on the reduction and the poor heat resistance.

The above results reveal that the provision of both the spray coated layer and the protective layer is effective in obtaining an oxygen concentration detecting device which has an improved heat resistance and a good effect on the reduction. As a matter of course, it is not necessary to form a thick spray coated layer as in prior art wherein a plasma spray coated layer alone is formed.

EXAMPLE 3

In the same manner as in Example 1, the detecting devices of sample Nos. 31 to 56 were made while changing the particle sizes RA and RB of the fine and coarse particles, the value of RB/RA, the content of the fine particles relative to the total of the fine and coarse particles, WA/W, the porosity, e, the average pore size, d, and the thickness, L. These parameters for the respective samples are indicated in Tables 3, 4, 6 and 7. For reference, an oxygen concentration detecting device which had a plasma spray coated layer as the protective layer was also provided as sample No. 57.

These sample Nos. 31 to 57 were evaluated in the same manner as in Example 1. The results of the evaluation are shown in Tables 5 and 8 provided that the evaluation of the resistance to poisoning is described in Example 5 appearing hereinafter.

TABLE 3

| Sample No. | RA (μm) | RB (μm) | RB/RA | WA/W (%) |
|---|---|---|---|---|
| 31 | 0.3 | 10 | 33 | 20 |
| 32 | 0.3 | 10 | 33 | 30 |
| 33 | 0.3 | 10 | 33 | 40 |
| 34 | 0.3 | 10 | 33 | 60 |
| 35 | 0.3 | 10 | 33 | 80 |
| 36 | 0.2 | 10 | 50 | 0 |
| 37 | 0.2 | 10 | 50 | 10 |
| 38 | 0.2 | 10 | 50 | 15 |
| 39 | 0.2 | 10 | 50 | 20 |
| 40 | 0.2 | 10 | 50 | 30 |
| 41 | 0.2 | 10 | 50 | 40 |
| 42 | 0.2 | 10 | 50 | 60 |
| 43 | 0.2 | 10 | 50 | 80 |
| 44 | 0.1 | 10 | 100 | 20 |
| 45 | 0.1 | 10 | 100 | 30 |
| 46 | 0.1 | 10 | 100 | 40 |
| 47 | 0.1 | 10 | 100 | 60 |
| 48 | 0.1 | 10 | 100 | 80 |

TABLE 4

| | | | Protective Layer | | | |
|---|---|---|---|---|---|---|
| | | | | $(\epsilon \times d)/L$ | | |
| No. | Porosity $\epsilon$ (%) | Average Pore Size d (μm) | Thickness L 100 μm | Thickness L 200 μm | Thickness L 300 μm | $\epsilon \times d$ |
| 31 | 24 | 0.11 | $26 \times 10^{-5}$ | $13 \times 10^{-5}$ | $8.7 \times 10^{-5}$ | $26 \times 10^{-3}$ |
| 32 | 22 | 0.09 | $20 \times 10^{-5}$ | $10 \times 10^{-5}$ | $6.7 \times 10^{-5}$ | $20 \times 10^{-3}$ |
| 33 | 25 | 0.10 | $25 \times 10^{-5}$ | $13 \times 10^{-5}$ | $8.3 \times 10^{-5}$ | $25 \times 10^{-3}$ |
| 34 | 30 | 0.12 | $36 \times 10^{-5}$ | $18 \times 10^{-5}$ | $12 \times 10^{-5}$ | $36 \times 10^{-3}$ |
| 35 | 45 | 0.12 | $54 \times 10^{-5}$ | $27 \times 10^{-5}$ | $18 \times 10^{-5}$ | $54 \times 10^{-3}$ |
| 36 | 46 | 3.00 | $1380 \times 10^{-5}$ | $690 \times 10^{-5}$ | $460 \times 10^{-5}$ | $1380 \times 10^{-3}$ |
| 37 | 30 | 0.34 | $1020 \times 10^{-5}$ | $540 \times 10^{-5}$ | $340 \times 10^{-5}$ | $1020 \times 10^{-3}$ |
| 38 | 25 | 0.10 | $25 \times 10^{-5}$ | $13 \times 10^{-5}$ | $8.3 \times 10^{-5}$ | $25 \times 10^{-3}$ |
| 39 | 22 | 0.05 | $11 \times 10^{-5}$ | $5.5 \times 10^{-5}$ | $3.7 \times 10^{-5}$ | $11 \times 10^{-3}$ |
| 40 | 18 | 0.04 | $7.2 \times 10^{-5}$ | $3.6 \times 10^{-5}$ | $2.4 \times 10^{-5}$ | $7.2 \times 10^{-3}$ |
| 41 | 23 | 0.04 | $9.2 \times 10^{-5}$ | $4.8 \times 10^{-5}$ | $3.1 \times 10^{-5}$ | $9.2 \times 10^{-3}$ |
| 42 | 32 | 0.05 | $16 \times 10^{-5}$ | $8.0 \times 10^{-5}$ | $5.3 \times 10^{-5}$ | $16 \times 10^{-3}$ |
| 43 | 48 | 0.05 | $24 \times 10^{-5}$ | $12 \times 10^{-5}$ | $8.0 \times 10^{-5}$ | $24 \times 10^{-3}$ |
| 44 | 22 | 0.04 | $8.8 \times 10^{-5}$ | $4.4 \times 10^{-5}$ | $2.9 \times 10^{-5}$ | $8.8 \times 10^{-3}$ |
| 45 | 14 | 0.03 | $4.2 \times 10^{-5}$ | $2.1 \times 10^{-5}$ | $1.4 \times 10^{-5}$ | $4.2 \times 10^{-3}$ |
| 46 | 23 | 0.03 | $6.9 \times 10^{-5}$ | $3.5 \times 10^{-5}$ | $2.3 \times 10^{-5}$ | $6.9 \times 10^{-3}$ |
| 47 | 40 | 0.04 | $16 \times 10^{-5}$ | $8.0 \times 10^{-5}$ | $5.3 \times 10^{-5}$ | $16 \times 10^{-3}$ |
| 48 | 50 | 0.04 | $20 \times 10^{-5}$ | $10 \times 10^{-5}$ | $6.7 \times 10^{-5}$ | $20 \times 10^{-3}$ |

TABLE 5

| | Effect on Gas Passage Reduction | | | Resistance to |
|---|---|---|---|---|
| No. | 100 μm | 200 μm | 300 μm | Poisoning |
| 31 | good | good | excellent | good |
| 32 | good | good | excellent | good |
| 33 | good | good | excellent | good |
| 34 | bad | good | good | good |
| 35 | bad | good | good | good |
| 36 | bad | bad | bad | good |
| 37 | bad | bad | bad | good |
| 38 | good | excellent | excellent | good |
| 39 | good | excellent | excellent | good |
| 40 | excellent | excellent | excellent | good |
| 41 | excellent | excellent | excellent | good |
| 42 | good | excellent | excellent | good |
| 43 | good | good | excellent | good |
| 44 | excellent | excellent | excellent | good |
| 45 | excellent | excellent | excellent | bad |
| 46 | excellent | excellent | excellent | good |
| 47 | good | excellent | excellent | good |
| 48 | good | good | excellent | good |

TABLE 6

| Sample No. | RA (μm) | RB (μm) | RB/RA | WA/W (%) |
|---|---|---|---|---|
| 49 | 1 | 10 | 10 | 30 |
| 50 | 0.5 | 10 | 20 | 30 |
| 51 | 0.2 | 5 | 25 | 30 |
| 52 | 0.2 | 3 | 15 | 30 |
| 53 | 0.2 | 1 | 5 | 30 |
| 54 | 0.1 | 5 | 50 | 30 |
| 55 | 0.1 | 3 | 30 | 30 |
| 56 | 0.1 | 1 | 10 | 30 |
| 57 | plasma spray coated layer | | | |
| 58 | plasma spray coated layer + trap layer | | | |

TABLE 7

| | | | | $(\epsilon \times d)/L$ | | |
|---|---|---|---|---|---|---|
| No. | Porosity $\epsilon$ (%) | Average Pore Size d (μm) | Thickness L 100 μm | Thickness L 200 μm | Thickness L 300 μm | $\epsilon = d$ |
| 49 | 30 | 0.3 | $90 \times 10^{-5}$ | $45 \times 10^{-5}$ | $30 \times 10^{-5}$ | $90 \times 10^{-3}$ |
| 50 | 26 | 0.15 | $39 \times 10^{-5}$ | $20 \times 10^{-5}$ | $13 \times 10^{-5}$ | $39 \times 10^{-3}$ |
| 51 | 25 | 0.04 | $10 \times 10^{-5}$ | $5.0 \times 10^{-5}$ | $3.3 \times 10^{-5}$ | $10 \times 10^{-3}$ |
| 52 | 40 | 0.05 | $20 \times 10^{-5}$ | $10 \times 10^{-5}$ | $6.7 \times 10^{-5}$ | $20 \times 10^{-3}$ |
| 53 | 55 | 0.06 | $33 \times 10^{-5}$ | $16 \times 10^{-5}$ | $11 \times 10^{-5}$ | $33 \times 10^{-3}$ |
| 54 | 14 | 0.03 | $4.2 \times 10^{-5}$ | $2.1 \times 10^{-5}$ | $1.4 \times 10^{-5}$ | $4.2 \times 10^{-3}$ |
| 55 | 40 | 0.03 | $12 \times 10^{-5}$ | $6.0 \times 10^{-5}$ | $4.0 \times 10^{-5}$ | $12 \times 10^{-3}$ |
| 56 | 55 | 0.04 | $22 \times 10^{-5}$ | $11 \times 10^{-5}$ | $7.3 \times 10^{-5}$ | $22 \times 10^{-3}$ |
| 57 | 10 | 0.04 | $9.2 \times 10^{-5}$ | $4.8 \times 10^{-5}$ | $3.1 \times 10^{-5}$ | $9.2 \times 10^{-3}$ |
| 58 | 10 | 0.04 | $9.2 \times 10^{-5}$ | $4.8 \times 10^{-5}$ | $3.1 \times 10^{-5}$ | $30 \times 10^{-3}$ |

TABLE 8

| | Effect on Gas Passage Reduction | | | Resistance to |
|---|---|---|---|---|
| No. | 100 μm | 200 μm | 300 μm | Poisoning |
| 49 | bad | bad | good | good |
| 50 | bad | good | good | good |
| 51 | good | excellent | excellent | good |
| 52 | good | good | excellent | good |
| 53 | bad | good | good | good |
| 54 | excellent | excellent | excellent | bad |
| 55 | good | excellent | excellent | good |
| 56 | good | good | excellent | good |
| 57 | good | excellent | excellent | bad |
| 58 | good | excellent | excellent | good |

The results shown in Tables 5 and 8 reveal that the sample Nos. 31 to 33, 38 to 48, 51, 52 and 54 to 56 which have a value of $(\epsilon \times d)/L$ ranging from $2.0 \times 10^{-5}$ to $30 \times 10^{-3}$ exhibit the effect on the reduction substantially equal to or better than that of the sample No. 57 which has the plasma spray coated layer as in the prior art.

Especially, the sample Nos. 39 to 41 and 44 to 46 are so small in porosity and average pore size that a thin protective layer is enough to provide a good effect on the gas passage reduction.

On the other hand, with the sample Nos. 34, 35, 49 and 50 which have a great average pore size and with the sample No. 53 having a great porosity, it is necessary to make a thick protective layer. By this, there can be obtained the effect on the reduction almost equal to that of the sample No. 57 having the protective layer formed by the plasma spray coating.

With the sample Nos. 36, 37 which have both great porosity and great average pore size, a satisfactory effect on the reduction cannot be attained even when the protective layer is formed in a thickness as great as 300 μm.

EXAMPLE 4

In the same manner as in Example 2, the oxygen concentration detecting devices of sample Nos. 60 to 68 were made wherein a plasma spray coated layer formed on an outer electrode. The thickness, the porosity and the average pore size of the plasma spray coated layer are shown in Table 9. The particulars of the protective layer including the particle sizes RA and RB of the fine particles and the coarse particles, the value of RB/RA, the porosity, the average pore size and the thickness in the respective samples are shown in Table 10.

For comparison, sample Nos. 59 and 71 which had no spray coated layer were also provided, along with sample Nos. 69 to 71 having no protective layer.

These samples were evaluated in the same manner as in Example 1.

The heat resistance was evaluated in the same manner as in Example 2.

The results are shown in Table 11.

TABLE 9

| | Plasma Spray Coated Layer | | |
|---|---|---|---|
| Sample No. | Thickness (μm) | Porosity (%) | Average Pore Size (μm) |
| 59 | 0 | — | — |
| 60 | 10 | 10 | 0.15 |
| 61 | 30 | 10 | 0.15 |
| 62 | 30 | 10 | 0.15 |
| 63 | 50 | 10 | 0.15 |
| 64 | 50 | 10 | 0.15 |
| 65 | 50 | 10 | 0.15 |
| 66 | 50 | 10 | 0.15 |
| 67 | 50 | 10 | 0.15 |
| 68 | 50 | 10 | 0.15 |
| 69 | 100 | 10 | 0.15 |
| 70 | 200 | 10 | 0.15 |
| 71 | 0 | — | — |

TABLE 10

| | | | | | Protective Layer | | | | |
|---|---|---|---|---|---|---|---|---|---|
| Sample No. | RA (μm) | RB (μm) | RB/RA | WA/W (%) | Porosity, $\epsilon$ (μm) | Average Particle Size, d (μm) | Thickness, L (μm) | $\epsilon \times d/L$ | $\epsilon = d$ |
| 59 | 0.2 | 10 | 50 | 30 | 18 | 0.04 | 200 | $3.6 \times 10^{-5}$ | $7.2 \times 10^{-5}$ |
| 60 | 0.2 | 10 | 50 | 30 | 18 | 0.04 | 200 | $3.5 \times 10^{-5}$ | $7.2 \times 10^{-5}$ |
| 61 | 0.2 | 10 | 50 | 30 | 18 | 0.04 | 150 | $4.4 \times 10^{-5}$ | $7.2 \times 10^{-5}$ |
| 62 | 0.2 | 10 | 50 | 30 | 18 | 0.04 | 100 | $6.3 \times 10^{-5}$ | $7.2 \times 10^{-5}$ |
| 63 | 0.1 | 10 | 100 | 30 | 14 | 0.03 | 100 | $3.7 \times 10^{-5}$ | $4.2 \times 10^{-5}$ |
| 64 | 0.1 | 10 | 100 | 30 | 14 | 0.03 | 50 | $6.6 \times 10^{-5}$ | $4.2 \times 10^{-5}$ |
| 65 | 0.2 | 10 | 50 | 30 | 18 | 0.04 | 100 | $5.8 \times 10^{-5}$ | $7.2 \times 10^{-5}$ |
| 66 | 0.2 | 10 | 50 | 30 | 18 | 0.04 | 50 | $9.7 \times 10^{-5}$ | $7.2 \times 10^{-5}$ |
| 67 | 0.3 | 10 | 33 | 30 | 22 | 0.09 | 100 | $11.9 \times 10^{-5}$ | $19.8 \times 10^{-5}$ |
| 68 | 0.3 | 10 | 33 | 20 | 24 | 0.11 | 100 | $14.0 \times 10^{-5}$ | $26.4 \times 10^{-5}$ |
| 69 | — | — | — | — | — | — | 0 | $15.0 \times 10^{-5}$ | $15.0 \times 10^{-5}$ |
| 70 | — | — | — | — | — | — | 0 | $7.5 \times 10^{-5}$ | $15.0 \times 10^{-5}$ |
| 71 | — | — | — | — | — | — | 0 | — | — |

TABLE 11

| Sample No. | Heat Resistance | Effect on Gas Passage Reduction | Resistance to Poisoning |
| --- | --- | --- | --- |
| 59 | moderate | excellent | good |
| 60 | moderate | excellent | good |
| 61 | good | excellent | good |
| 62 | good | excellent | good |
| 63 | good | excellent | bad |
| 64 | good | excellent | bad |
| 65 | good | excellent | good |
| 66 | good | excellent | good |
| 67 | good | good | good |
| 68 | good | good | good |
| 69 | good | good | good |
| 70 | good | excellent | good |
| 71 | bad | bad | bad |

From the above results, it will be seen that the sample Nos. 61 to 68 of the invention which has a plasma spray coated layer exhibit a good or excellent effect on the gas passage reduction along with a good heat resistance.

In view of the results of the sample Nos. 59, 60 wherein any plasma spray coated layer is not formed (No. 59) and a thin spray coated layer is formed (No. 60), these samples are slightly inferior to the sample Nos. 61 to 68 with respect to the heat resistance.

From the results of the sample Nos. 69, 70, it will be seen that when the spray coated layer is made thick, this layer plays a role similar to a protective layer, and a good effect on the reduction and an excellent heat resistance can be obtained. However, the formation of a thick plasma spray coated layer has the problem that the plasma spay coating involves a poor yield of material along with a difficulty in obtaining a stable performance.

The sample No. 71 which had neither any spray coated layer nor any protective layer is found to be poor in both the effect on gas passage reduction and the heat resistance.

From the above, it will be apparent that the formation of both the spray coated layer (which is relatively thin on comparison with the prior art) and the protective layer is effective in improving the capability of appropriately reducing gas passage toward the outer electrode and the heat resistance.

EXAMPLE 5

The sample Nos. 31 to 71 made in Example 3 and 4 were used to form a trap layer on the protective layer. The trap layer was formed by mixing 45 parts by weight of $\gamma$-$Al_2O_3$, 2 parts by weight of alumina sol as an inorganic binder, and 53 parts by weight of water to obtain a slurry, and applying the slurry on the surface of the protective layer by dipping, followed by heating to a temperature of 700° C. for 1 hour.

The samples which were formed with such a trap layer as mentioned above and subjected to a poisoning test included the sample Nos. 31 to 56 having a protective layer thickness of 200 μm. The sample No. 57 had only a protective layer formed by plasma spray coating without further formation of any trap layer. The sample Nos. 69, 70 which had no protective layer were formed with the trap layer on the spray coated layer. The sample No. 71 had no protective layer. In this case, the trap layer was formed directly on the surface of the outer electrode.

The poisoning durability was determined by subjecting each sample to an accelerated poisoning durability test wherein each sample was set in an exhaust gas pipe, and 5 wt % of an engine oil containing poisoning components was added to a gasoline fuel used for this test. The engine was idled for 30 minutes, after which it was rotated at a frequency of 4000 r.p.m., for 30 minutes, followed by continuously repeating this operation over 100 hours.

The engine used for the test was a 2000 cc series four cylinder engine equipped with a fuel injector.

The poisoning durability was judged from the variation in responsibility prior to and after the accelerated poisoning durability test. More particularly, when an initial response time is taken as $T_o$ and a response time after the durability test is taken as T, a variation of $(T-T_o)/T_o$ is calculated. If this variation is less than 0.5, such a sample is evaluated as good and when the variation is 0.5 or above, a sample is evaluated as bad. The results are shown in Tables 5, 8 and 11.

As will be apparent from these results, when $\epsilon > 15\%$ and $\epsilon \times d$ is not less than $5.0 \times 10^{-3}$, good poisoning durability is obtained as compared to that of sample No. 58 wherein the trap layer is formed on a known protective layer.

On the other hand, with the sample Nos. 45, 54, 57, 63 and 64 wherein $\epsilon < 15\%$ or the value of $\epsilon \times d$ is less than $5.0 \times 10^{-3}$, the variation was so great that the poisoning resistance is poor.

The oxygen concentration detecting devices illustrated in the foregoing Examples 1 to 5 serve as so-called "λ sensor" for detecting a theoretical air-to-fuel ratio in internal combustion engines of automotive vehicles. The protective layer in the device of the invention may be used as a diffusion resistant layer in oxygen concentration detecting devices of the critical current type, i.e. lean sensors, or in full-range air-to-fuel ratio sensors.

What is claimed is:

1. An oxygen concentration detecting device which comprises a solid electrolyte body, an inner electrode formed on an inner side of the solid electrolyte body and exposed to a reference gas fed from outside, an outer electrode formed on an outer side of the solid electrolyte body and exposed to a gas to be measured, and a protective layer formed on the outer electrode, wherein the protective layer has a structure which comprises coarse particles and fine particles packed in spaces formed among the coarse particles and wherein the coarse particles and the fine particles are mutually bonded through a metal oxide derived from an inorganic binder while substantially keeping original forms of the coarse particles and the fine particles, a ratio of an average particle size, RB, of the coarse particles to an average particle size, RA, of the fine particles is such that the value of RB/RA is 30:1 or above, and a content, WA, of the fine particles in the protective layer based on the total, W, of the content, WA, of the fine particles and the content, WB, of the coarse particles on the weight basis is in the range of 15 to 80%.

2. An oxygen concentration detecting device according to claim 1, wherein said coarse particles and said fine particles, respectively, consist of at least one member selected from the group consisting of $Al_2O_3$, $ZrO_2$, $MgO \cdot Al_2O_3$ spinel and mullite.

3. An oxygen concentration detecting device according to claim 1, wherein said fine particles have an average particle size of from 0.1 μm to less than 1 μm, and said coarse particles have an average particle size of from 3 to 50 μm.

4. An oxygen concentration detecting device according to claim 1, further comprising a plasma spray coated layer between said outer electrode and said protective layer.

5. An oxygen concentration detecting device according to claim 4, wherein said plasma spray coated layer has a thickness of from 30 to 100 μm.

6. An oxygen concentration detecting device which comprises a solid electrolyte body, an inner electrode formed on an inner side of the solid electrolyte body and exposed to a reference gas fed from outside, an outer electrode formed on an outer side of the solid electrolyte body and exposed to a gas to be measured, and a protective layer formed on the outer electrode, wherein the protective layer has a structure which consists of coarse particles and fine particles packed in spaces formed among the coarse particles and wherein the coarse particles and the fine particles are mutually bonded through a metal oxide derived from an inorganic binder while substantially keeping original forms of the coarse particles and the fine particles, the protective layer being formed by a process which comprises applying, onto the outer electrode, a slurry obtained by dispersing heat-resistant coarse particles and heat-resistant fine particles in a liquid medium, drying the thus applied slurry, and baking the resultant layer, the layer having a ratio of an average particle size, RB, of the coarse particles to an average particle size, RA, of the fine particles of 30:1 or above provided that the value of RB/RA is 10 or above when the value of $(\epsilon \times d)/L$ is within a range of $2.0 \times 10^{-5}$ to $30 \times 10^{-5}$ wherein $\epsilon$, d and L are, respectively, a porosity, an average pore size by μm and a thickness by μm of the protective layer, and a content, WA, of the fine particles in the protective layer based on the total, W, of the content, WA, of the fine particles and the content, WB, of the coarse particles on the weight basis is in the range of 15 to 80%.

7. An oxygen concentration detecting device according to claim 6, wherein the porosity, $\epsilon$, is within a range of 50% or below.

8. An oxygen concentration detecting device according to claim 6, wherein the average pore size, d, in said protective layer is within a range of from 0.01 to 0.3 μm.

9. An oxygen concentration detecting device according to claim 6, wherein the value of RB/RA is 10 or above, provided that the value of $\epsilon$ is such that $15\% < \epsilon < 50\%$, and the value of $(\epsilon \times d)$ is within a range of $5 \times 10^{-3}$ or above.

10. An oxygen concentration detecting device according to claim 6, wherein the protective layer is baked at a temperature ranging from 500° to 1000° C.

11. An oxygen concentration detecting device according to claim 6, wherein further comprising a plasma spray coated layer formed on the outer electrode by plasma spray coating a heat-resistant metal oxide prior to the formation of said protective layer.

12. An oxygen concentration detecting device according to claim 11, wherein said plasma spray coated layer is formed in a thickness of from 30 to 100 μm.

13. A method for making an oxygen concentration detecting device which comprises a solid electrolyte body, an inner electrode formed on an inner side of the solid electrolyte body and exposed to air fed from outside, an outer electrode formed on an outer side of the solid electrolyte body and exposed to a gas to be measured, and a protective layer formed on the outer electrode, wherein the protective layer has a structure which consists of coarse particles and fine particles packed in spaces formed among the coarse particles, the method comprising depositing a slurry obtained by dispersing heat-resistant coarse particles and fine particles in a liquid medium therefor on the outer electrode, drying the deposited slurry, and baking the resultant layer wherein the protective layer has such a structure that the coarse particles and the fine particles are mutually bonded through a metal oxide derived from an inorganic binder while substantially keeping original forms of the coarse particles and the fine particles.

14. A method according to claim 13, wherein said protective layer has a ratio of an average particle size, RB, of the coarse particles to an average particle size, RA, of the fine particles of 30:1 or above provided that the value of RB/RA is 10 or above when the value of $(\epsilon \times d)/L$ is within a range of $2.0 \times 10^{-5}$ to $30 \times 10^{-5}$ wherein $\epsilon \times$, d and L are, respectively, a porosity, an average pore size by μm and a thickness by μm of the protective layer, and a content, WA, of the fine particles in the protective layer based on the total, W, of the content, WA, of the fine particles and the content, WB, of the coarse particles on the weight basis is in the range of 15 to 80%.

15. A method according to claim 14, wherein the porosity, $\epsilon$, is within a range of 50% or below.

16. A method according to claim 14, wherein the average pore size, d, in said protective layer is within a range of from 0.01 to 0.3 μm.

17. A method according to claim 14, wherein the value of RB/RA is 10 or above, provided that the value of $\epsilon$ is such that $15\% < \epsilon < 50\%$, and the value of $(\epsilon \times d)$ is within a range of $5 \times 10^{-3}$ or above.

18. A method according to claim 14, wherein the baking is carried out at a temperature ranging from 500° to 1000° C.

19. A method according to claim 14, wherein the process further comprising forming a plasma spray coated layer on the outer electrode by plasma spray coating a heat-resistant metal oxide prior to the formation of said protective layer.

20. A method according to claim 19, wherein said plasma spray coated layer is formed in a thickness of from 30 to 100 μm.

* * * * *